(12) United States Patent
Becker et al.

(10) Patent No.: US 9,733,240 B2
(45) Date of Patent: Aug. 15, 2017

(54) GENERAL STRATEGY FOR ANTIBODY LIBRARY SCREENING

(71) Applicant: Merck Patent GmbH, Darmstadt (DE)

(72) Inventors: Stefan Becker, Darmstadt (DE); Tim Heiseler, Rossdorf (DE); Alexander Maass, Darmstadt (DE); Harald Kolmar, Muehltal-Trautheim (DE)

(73) Assignee: Merck Patents GmbH, Darmstadt (DE)

( * ) Notice: Subject to any disclaimer, the term of this patent is extended or adjusted under 35 U.S.C. 154(b) by 633 days.

(21) Appl. No.: 14/361,358

(22) PCT Filed: Dec. 14, 2012

(86) PCT No.: PCT/EP2012/005162
§ 371 (c)(1),
(2) Date: May 29, 2014

(87) PCT Pub. No.: WO2013/087215
PCT Pub. Date: Jun. 20, 2013

(65) Prior Publication Data
US 2014/0357514 A1   Dec. 4, 2014

(30) Foreign Application Priority Data
Dec. 16, 2011  (EP) .................................... 11009901

(51) Int. Cl.
| C40B 30/08 | (2006.01) |
| G01N 33/543 | (2006.01) |
| C12N 15/10 | (2006.01) |
| G01N 33/532 | (2006.01) |
| G01N 33/542 | (2006.01) |
| G01N 33/554 | (2006.01) |

(52) U.S. Cl.
CPC ... *G01N 33/54353* (2013.01); *C12N 15/1037* (2013.01); *C12N 15/1086* (2013.01); *G01N 33/532* (2013.01); *G01N 33/542* (2013.01); *G01N 33/554* (2013.01); *C40B 30/08* (2013.01)

(58) Field of Classification Search
None
See application file for complete search history.

(56) References Cited

U.S. PATENT DOCUMENTS
2002/0004215 A1   1/2002  Osbourn et al.

FOREIGN PATENT DOCUMENTS
WO   WO 2004/111259 A2   12/2004

OTHER PUBLICATIONS

Bobrow, M.N. et al., "The use of catalyzed reporter deposition as a means of signal amplification in a variety of formats", J. Immunol. Meth., 1992, vol. 150, pp. 145-149.

(Continued)

*Primary Examiner* — Christian Boesen
(74) *Attorney, Agent, or Firm* — Olson & Cepurtis, Ltd.

(57) ABSTRACT

A generally applicable method for the selective covalent attachment of a reporter molecule to a replicating entity that allows one to obtain specific binders from a single round of library screening is disclosed. For example, selective biotinylation of phage particles and yeast cells displaying a binder to any given target can be achieved via application of a coupled enzyme reaction that includes a peroxidase, an oxidase and a catalase.

13 Claims, 14 Drawing Sheets

(56) References Cited

OTHER PUBLICATIONS

Becker, S. et al., "Ultrahigh-throughput screening to identify *E coli* cells expressing functionally active enzymes on their surface", ChemBioChem, 2007, vol. 8, pp. 943-949.

Sudhir, P. et al., "Phosphonate ester probes for proteolytic antibodies", J. Biol. Chem., Jul. 27, 2001, vol. 276, No. 30, pp. 28314-28320.

A

B

A

B

SEQUENCE LISTING

```
<160> NUMBER OF SEQ ID NOS: 2

<210> SEQ ID NO 1
<211> LENGTH: 35
<212> TYPE: PRT
<213> ORGANISM: Artificial Sequence
<220> FEATURE:
<223> OTHER INFORMATION: Synthetic

<400> SEQUENCE: 1

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Glu Val Ser Ala
            20                  25                  30

Leu Glu Lys
        35

<210> SEQ ID NO 2
<211> LENGTH: 35
<212> TYPE: PRT
<213> ORGANISM: Artificial Sequence
<220> FEATURE:
<223> OTHER INFORMATION: Synthetic

<400> SEQUENCE: 2

Lys Val Ser Ala Leu Lys Glu Lys Val Ser Ala Leu Lys Glu Lys Val
1               5                   10                  15

Ser Ala Leu Lys Glu Lys Val Ser Ala Leu Lys Glu Lys Val Ser Ala
            20                  25                  30

Leu Lys Glu
        35
```

GENERAL STRATEGY FOR ANTIBODY LIBRARY SCREENING

CROSS-REFERENCE TO RELATED APPLICATIONS

This application is a U.S. National Phase of PCT/EP2012/005162, filed Dec. 14, 2012, which claims priority of European Patent Application No. 11009901.7, filed Dec. 16, 2011, each of which is incorporated herein by reference.

INCORPORATION OF SEQUENCE LISTING

Biological sequence information for this application is included in an ASCII text file, filed with the application, having the file name "MER145SEQ.txt", created on Apr. 5, 2017, and having a file size of 1,198 bytes, which is incorporated by reference.

The phage display technology was originally introduced by George Smith more than 25 years ago (Smith 1985) and has become an indispensable tool in molecular biotechnology to identify peptides and particularly antibody molecules with predefined binding characteristics from large libraries. Since then, many improvements have been reported and screening concepts are now available to identify binding molecules against virtually any target protein Bradbury et al. 2011) Moreover, in recent years bacterial and particularly yeast surface display have become increasingly popular alternatives for phage display library screening applications (Pepper et al., 2008, van Blois et al. 2011).

Library screening generally involves exposure of a population of binding molecules on the surface of a replicating entity and contacting them with an interaction partner of interest, which is in the case of antibody display an antigen molecule. The experimental setup is designed such that those phage particles or microbial cells displaying a target-specific antibody can be isolated from the population e.g. via biopanning or cell sorting. Ideally, a single round of screening would be required to obtain the desired protein variants. However, the enrichment of specific binders is limited by non-specific binding which requires recursive rounds of screening and amplification to obtain the best binders from the library (Vodnik et al. 2011). Particularly the first screening round is critical, since it can be expected for large libraries that specific binders constitute only a tiny fraction of the initial population such that non-specific binders largely dominate over those that interact specifically. As a consequence, conditions have to be carefully controlled and optimized for every single screening experiment that are stringent enough to remove non-specific binders but sufficiently mild to keep the target binding of specifically interacting library members intact (Liu et al. 2009).

Since the probability of obtaining high affinity binders increases with library size (Steiner, Forrer 2008) increasingly larger libraries have been established that can exceed $10^{10}$ different variants (Rothe et al. 2008, Brockmann et al. 2011). However, repeated amplification of libraries as it occurs in each screening round is known to reduce diversity and limits the number of candidates that can be identified in a library screening experiment. (Derda et al. 2011). As a consequence, it is highly desirable to reduce the number of screening rounds to a minimum, optimally to a single round. Conceptually, this can be achieved by setting up a method were the transient and relatively weak interaction of target and library member translates into covalent attachment of a labelling molecule that can be used as purification handle and allows for application of rather stringent conditions to remove non-specifically bound library members.

Catalysed reporter deposition (CARD) has been widely used in immune histochemistry for protein biotinylation (Bobrow et al., 1989, 1991, 1992). It relies on the horseradish peroxidase (HRP) mediated formation of a biotin tyramide radical that readily reacts with proteins in close proximity resulting in the formation of a covalent linkage between biotin and tyrosine residues on proteins (FIG. 1). To establish a selective biotinylation of phage or cell surface display library members to which a target molecule is bound, we make use of the fact that HRP mediated biotinylation requires the presence of hydrogen peroxide. The $^3$CARD system described here combines the activity of three different enzymes, namely a peroxidase, an oxidase and a catalase. First, HRP is coupled onto all members of a starting population, which is examplified for usage within the experimental setting of a phage display library (FIG. 1a). Phage biotinylation by HRP requires presence of biotin tyramide (FIG. 5) and of hydrogen peroxide. In the $^3$CARD setup $H_2O_2$ is generated by a second enzyme that is conjugated to the antigen of interest (FIG. 1b, c). Sugar oxidases as galactose or glucose oxidase catalyse the oxidation of sugars via electron transfer to oxygen which results in formation of hydrogen peroxide. Hydrogen peroxide is only generated at higher concentrations on those phage particles to which the antigen-oxidase complex is bound since the reaction mixture contains as a third enzyme catalase that very efficiently breaks down hydrogen peroxide. As a consequence $H_2O_2$ transfer to HRP and subsequent phage biotinylation should only occur for antigen binding phage that has the oxidase in close proximity to HRP. Specifically labelled phage can then be rescued via biopanning to immobilized streptavidin and subjected to very stringent wash conditions prior to phage infection of bacteria.

There is however no mention of CARD for enhancing the effectiveness of phage, bacterial or yeast display systems in the art.

There is a high need in the art to enhance such effectiveness. As explained above, isolation of specific binders is still highly empirical, and requires adaptation of the experimental setting basically for every specific setup comprising a given display system and a specific ligand.

Therefore, it was the object of the present invention to provide an efficient display system that i.a. allows for the reduction of selection/amplification steps required to isolate highly specific binders.

The present invention discloses a surprisingly easy to establish and highly efficient improvement of the display systems known in the art.

In a first embodiment the present invention relates to a new method for the isolation of specifically labelled replicating entities, said method comprising
  a) providing in a reaction mixture a collection of replicating entities displaying variants of a receptor molecule on their surface and having either a first or a second enzyme linked to said surface,
  b) adding to the mixture of step a) ligand molecules that are either linked to said first enzyme if said entities are linked to said second enzyme, or said ligands are linked to said second enzyme if said entities are linked to said first enzyme,
  c) adding to the reaction mixture a substrate for the second enzyme, the substrate being utilized by said second enzyme in an enzymatic reaction to produce a product that is utilized by said first enzyme to convert a cosubstrate of said first enzyme into a reactive marker molecule that physically links to the respective replicating entity, thereby specifically labelling the replication entity, and d) isolating the specifically labelled replicating entities.

In a preferred embodiment the reaction mixture of step a) comprises in addition a third enzyme, which enzyme is capable of decomposing excess product of said first and/or second enzyme.

In a further preferred embodiment the replicating entity is selected from the group consisting of a phage, a phagemid, or a cell.

In a further preferred embodiment the replicating entity is a yeast cell, preferably Saccharomyces cerevisiae.

In a further preferred embodiment the first enzyme is a peroxidase, preferably horseradish peroxidase, the second enzyme is an oxidase, preferably glucose oxidase, and the third enzyme is catalase.

In a further preferred embodiment the substrate of the second enzyme is glucose and the product is $H_2O_2$.

In a further preferred embodiment the cosubstrate of said first enzyme is a tyramide conjugated to a marker molecule.

In a further preferred embodiment the marker molecule is biotin, (2,4)-dinitrophenyl, fluorescein or digoxygenin derivative.

In a further preferred embodiment the tyramide is linked to the marker molecule by a cleavable linker, preferably a disulfide bond or a peptide sequence that can be cleaved by a protease.

In a further preferred embodiment the marker molecule is biotin, and the isolation step d) is accomplished by affinity chromatography on an avidin or streptavidin matrix.

In a further preferred embodiment the marker molecule is fluorescein or a fluorescent avidin or streptavidin bound biotin and the isolation step d) is accomplished by fluorescence activated cell sorting.

In a further preferred embodiment the marker molecule is biotin and the isolation comprises magnetic cell sorting through the aid of streptavidin or avidin coated paramagnetic particles bound to the biotin labelled entity.

A specially preferred embodiment of the present invention is a non-naturally occurring replicating entity that displays a variety of receptor molecules on its surface and has an enzyme coupled to its surface.

A further specially preferred embodiment of the present invention is a non-naturally occurring replicating entity of the preceding paragraph, the enzyme being selected from the group consisting of peroxidase or oxidase.

A further specially preferred embodiment of the present invention is the non-naturally occurring replicating entity of the preceding paragraph, wherein the receptor molecule is an antibody or an antibody derived fragment.

A further specially preferred embodiment of the present invention is a kit of parts comprising the non-naturally occurring replicating entity of the invention, a substrate, and a cosubstrate.

A further specially preferred embodiment of the present invention is the kit of the preceding paragraph, the entity being selected from the group consisting of a phage, a phagemid, or a cell, the cell preferably being a yeast cell, more preferably Saccharomyces cerevisiae, the receptor molecule being an antibody, the enzyme linked to the surface of the entity being glucose oxidase or horseradish peroxidase, the substrate being glucose and the cosubstrate being a tyramide coupled to a marker molecule, preferably biotin.

For example, to establish a selective biotinylation of phage or cell surface display library members to which a target molecule is bound, the present invention in one preferred embodiment makes use of the fact that horseradish peroxidase (HRP, E.C.1.11.1.7) mediated biotinylation requires the presence of hydrogen peroxide. The $^3$CARD system described here combines the activity of three different enzymes, namely a peroxidase, an oxidase and a catalase. First, HRP is coupled onto all members of a starting population, which is within the experimental setting of phage display library screening a population of phage particles (FIG. 1a). Phage biotinylation by HRP requires presence of biotin tyramide and of hydrogen peroxide. In the $^3$CARD setup $H_2O_2$ is generated by a second enzyme that is conjugated to the antigen of interest (FIG. 1b, c). Sugar oxidases as galactose or glucose oxidase catalyse the oxidation of sugars via electron transfer to oxygen which results in formation of hydrogen peroxide. Hydrogen peroxide is only generated at higher concentrations on those phage particles to which the antigen-oxidase complex is bound since the reaction mixture contains as a third enzyme catalase that very efficiently breaks down hydrogen peroxide. As a consequence $H_2O_2$ transfer to HRP and subsequent phage biotinylation only occurs for antigen binding phage that has the oxidase in close proximity to HRP. Specifically labelled phage can then be rescued via biopanning to immobilized streptavidin and subjected to very stringent wash conditions prior to phage infection of bacteria.

In the example part of the present patent the inventors describe the application of $^3$CARD for single domain antibody library screening and present straightforward methods for coupling HRP onto the phage surface and conjugating oxidase with target protein such that a combined enzyme reaction on phage results in selective biotinylation and isolation in a single round of screening.

For the phage display screening procedure described here to be functional, the inventors had to show that a coupled reaction of an oxidase and peroxidase can be performed on phage particles, where the hydrogen peroxide generated by an oxidase that is coupled to the phage surface via antigen/antibody interaction eventually leads to selective labelling of the bound phage and thereby to genotype phenotype coupling. In addition, a simple method for conjugation of the target protein of interest to an oxidase had to be established.

To address these points, a model experiment was performed that relies on the phage display of a camelid VHH single chain antibody fragment that selectively binds Pseudomonas aeruginosa LipH chaperon (Wilhelm et al. 2007). Presentation of the anti-LipH VHH domain on phage was achieved via genetic fusion of the VHH fragment to truncated pIII using phage display vector pAK200 (Habicht et al. 2007).

The invention is explained in part by the following figures:

FIG. 1 shows a general outline of the $^3$CARD phage display screening procedure. (a) covalent deposition of horseradish peroxidase (HRP) to the surface of phage particles that display a library of antibody variants (AB). (b,c) generation of hydrogen peroxide ($H_2O_2$) by antigen-oxidase conjugate (AgOx) and coupled reaction with HRP that converts biotin tyramide (BT) to a radical that becomes captured to the surface of phage.

FIG. 2 shows a coupled enzyme reaction on phage. (a) HRP coupling to the surface of phage particles. LipH protein was coupled to the wells of a microtiter plate. Phage displaying an anti-LipH VHH (☐LipH VHH) or unrelated protein to serve as a control were decorated with HRP (+HRP) and added to the wells (dark grey bars). Unconjugated ☐LipH VHH phage served as a control (light grey bar). For the undecorated anti-LipH-VHH phage, target protein binding of phage was verified by addition of a peroxidase conjugated anti pVIII antibody. HRP activity was detected by addition of TMB and measurement of absorbance at 450 nm. (b) oxidase mediated activation of HRP on phage. Wells of a microtiter plate were coated with LipH-GOase conjugate or as a control with bovine serum albumin (BSA), respectively. After addition of HRP decorated anti-LipH VHH phage (black bar) or control phage (white bar) and plate wash galactose was added and HRP activity was measured after addition of TMB at 450 nm. Error bars represent the standard deviation from three measurements.

FIG. 3 shows enrichment of binders via $^3$CARD screening. (a) phage ELISA for LipH binding of a 1:10,000 (white) and a 1:100,000 (grey) mixture of LipH binding phage to control phage before (round 0) and after screening rounds 1, 2, and 3. Phage binding to microtiter plate coated LipH was determined using an peroxidase-conjugated anti pVIII antibody and chromogenic HRP substrate via measurement of absorbance at 450 nm. Error bars show the standard deviation from three measurements. (b,c) PCR screen of individual phagemids obtained after screening round 2 using primers that flanks the gene fused to the pIII coding sequence. For the anti-LipH VHH presenting phage, a 676 bp fragment is expected, for the control phage that contains a smaller miniprotein encoding sequence, a 394 bp fragment is generated. P: phagemid DNA from anti-LipH VHH presenting phagemid that served as a PCR control.

FIG. 4 shows phage ELISA of 64 individual clones after $^3$CARD screening against the respective target. Microtiter plates were coated with the respective target protein Cetuximab, factor XIII, and Saglin, respectively. Phage binding was detected via addition of peroxidase-conjugated anti pVIII antibody using the chromogenic HRP substrate TMB and measurement of absorbance at 450 nm. Clones that have been selected for expression as soluble protein and $K_d$ determination are marked by an asterisk. The mean value of absorbance that is indicative of non-binding was determined from ten of the clones of each experiments with the lowest $OD_{450}$ values. Clones exceeding this value at least by a factor of 2.5 were considered to be potential target protein binders and were displayed as black bars.

Figure 8:
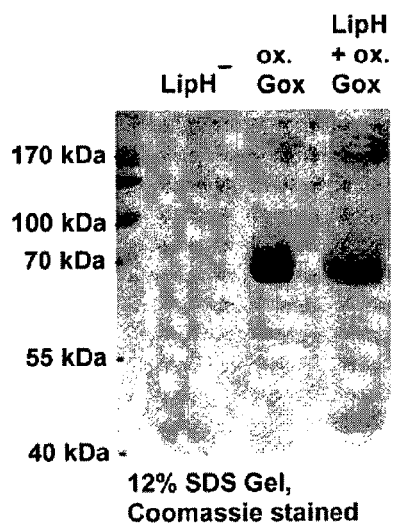

FIG. 8 shows a coomassie gel to verify the coupling of ox. GOX to LipH. In the first two rows the educts are shown (Glucoseoxidase 70 kDa, LipH 50 kDa). Presence of the resulting 170 kDa interaction product in row 3 was also verified by western blot (not shown).

Figure 9:
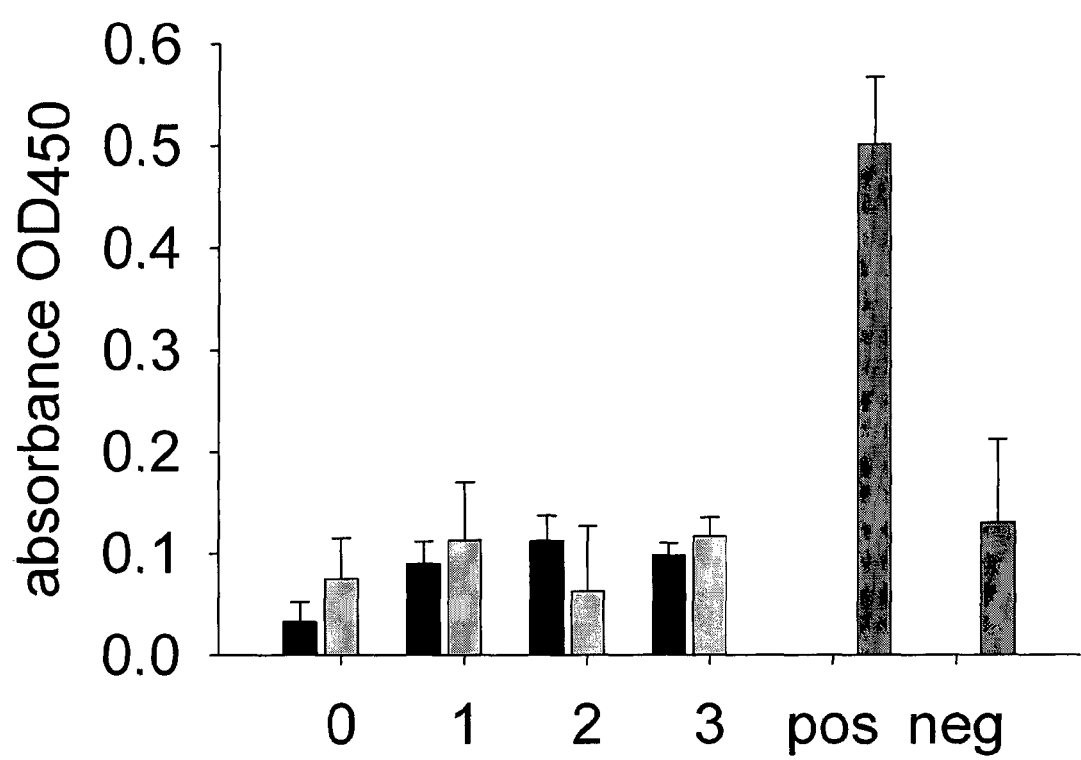

FIG. 9 shows phage ELISA of a mock $^3$CARD screening without addition of biotin tyramide (black bars) or galactose (grey bars), respectively. Screening was performed as described (see "Validation of genotype-phenotype coupling"), with the same mixing ratios of binding to nonbinding phages. No enrichment of binders could be detected by phage ELISA or PCR screen (0/10) after three panning rounds. Pos: phage ELISA using an anti-LipH phage which is able to bind to the coated LipH. neg: Background bining of a phage displaying an unrelated protein. Phage binding to microtiter plate coated LipH was determined using an peroxidase-conjugated anti pVIII antibody and measurement of the absorbance at 450 nm of a chromogenic HRP substrate. Experiments were done in triplicate.

Figure 10:
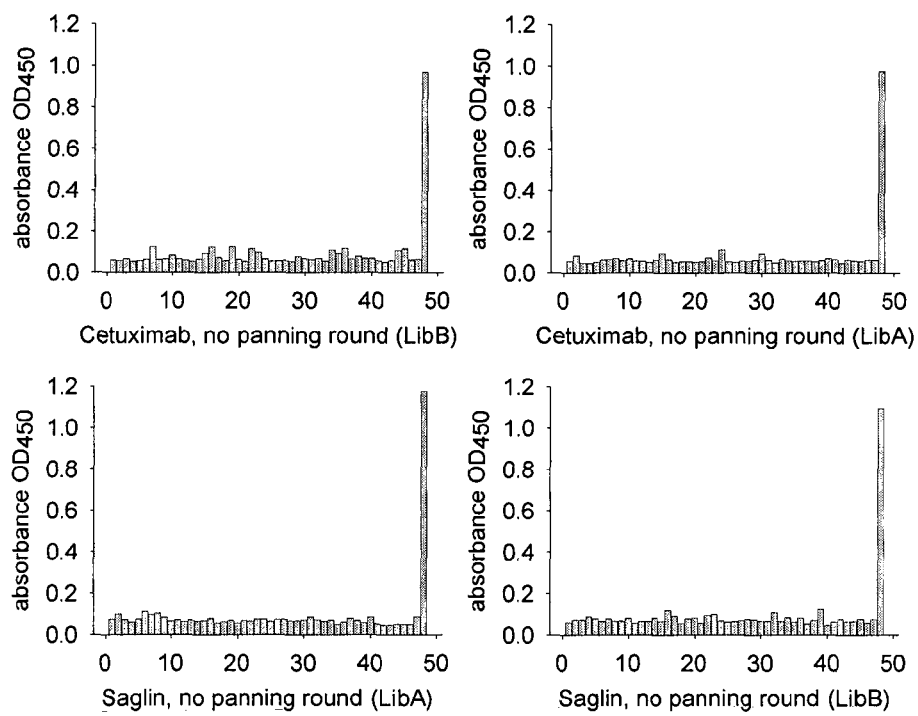

FIG. 10 shows phage ELISAs of 47 single clones of the initial library. As expected, no specific binders to target proteins Saglin and Cetuximab were detected in initial libraries LibA and LibB. As a positive control the already selected Cetuximab and Saglin binding phage were used (last well).

Figure 11:
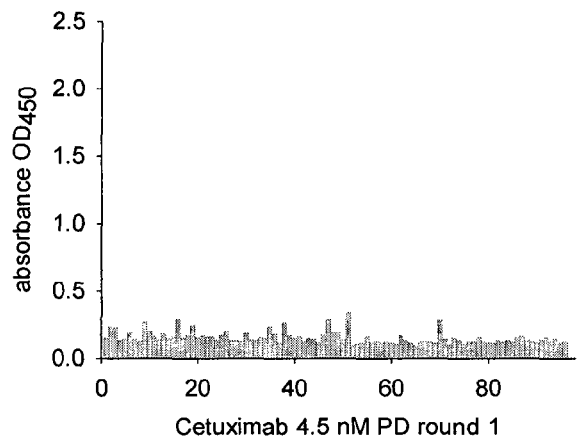
Figure 11:
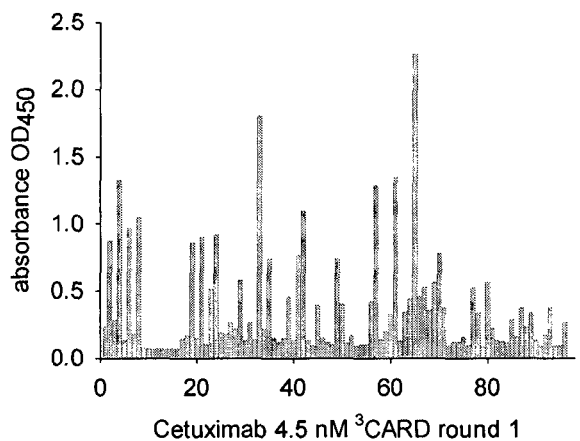

FIG. 11 shows single round screening of a phage library for binders of Cetuximab. A: state of the art screening, B: 3CARD screening. Clones giving ELISA signals >0.3 were considered as binders. A: 1 clones, B: 36 clones. PD: classical Phage Display screening.

Figure 12:
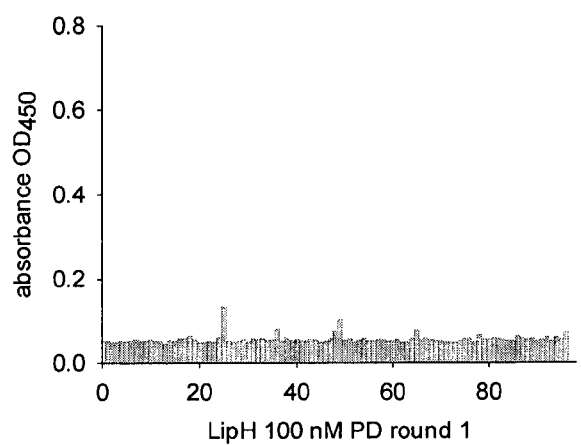
Figure 12:
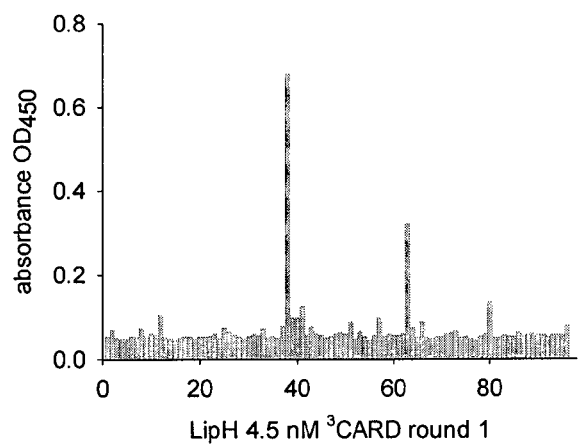

FIG. 12 shows single round screening of a phage library for binders of LipH. A: state of the art screening, B: 3CARD screening. Clones giving ELISA signals >0.2 were considered as binders. A: 0 clones, B: 2 clones. PD: classical Phage Display screening.

Figure 13:
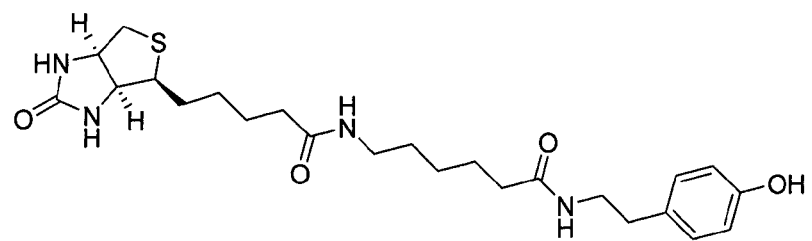
Figure 13:
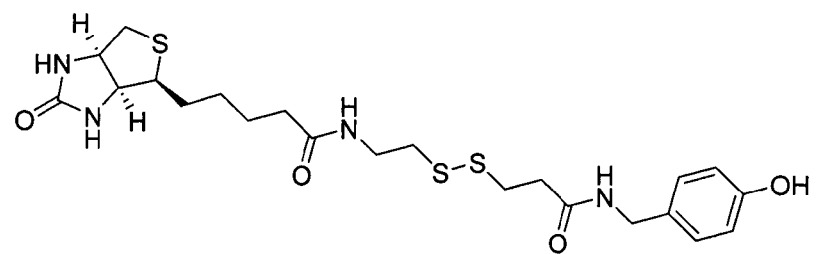

FIG. 13 shows the structure of Biotintyramide (A) respectively Biotintyramide with cleavable disulfide bond (B).

Figure 14:
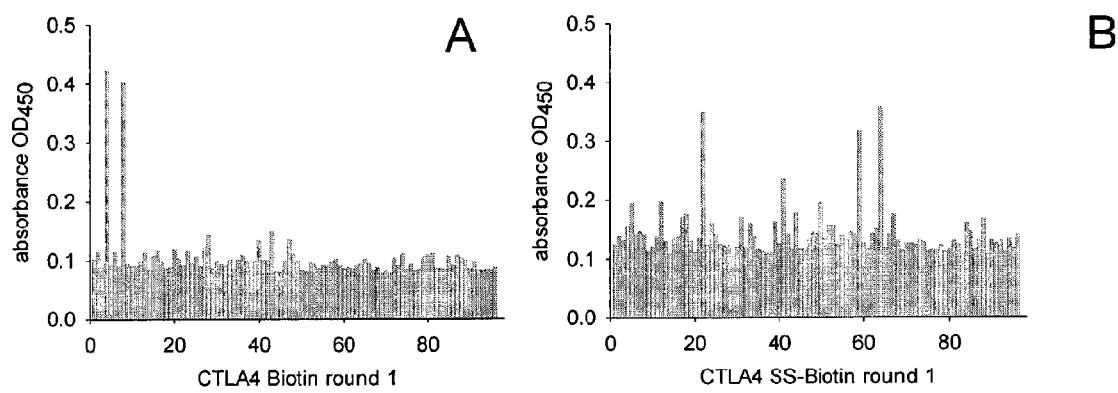

FIG. 14 shows screening of a phage library for binders of CTLA4. Left: Using biotin tyramide, right using biotin-SS-tyramide). Clones giving ELISA signals >0.2 were considered as binders. Left: 2 clones, right 4 clones.

Figure 15:
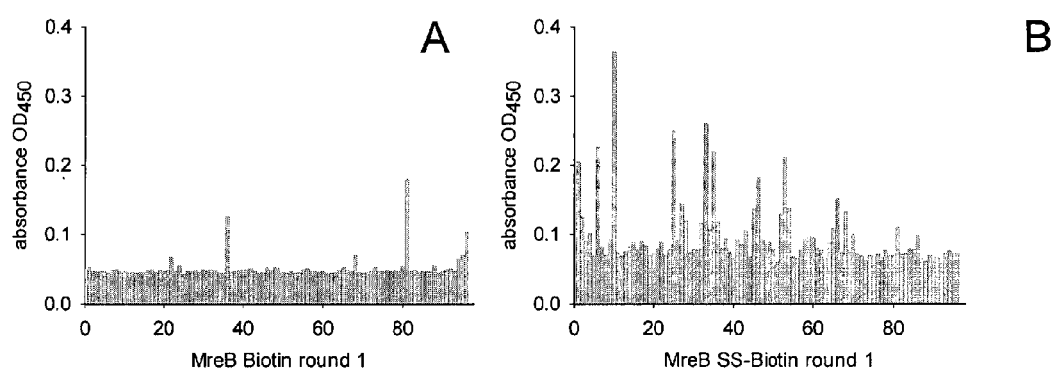

FIG. 15 shows screening of a phage library for binders of MreB. Left: Using biotin tyramide, right using biotin-SS-tyramide. Clones giving ELISA signals >0.15 were considered as binders. Left: 2 clones, right 8 clones.

Figure 16:
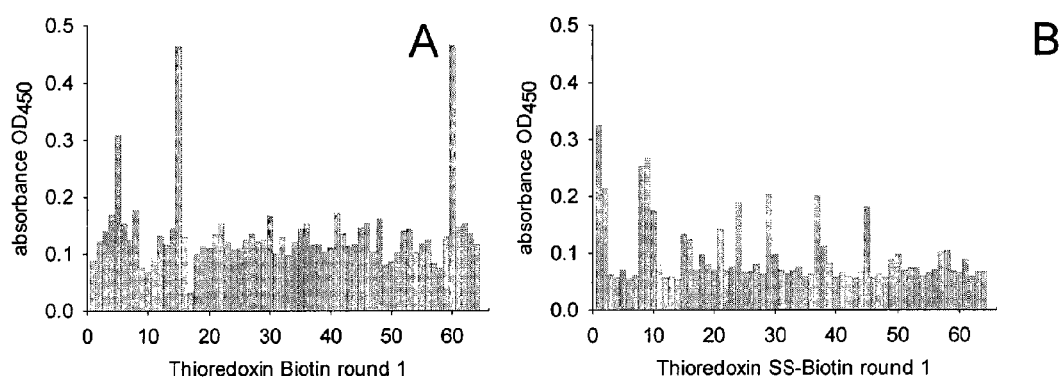

FIG. 16 shows screening of a phage library for binders of thioredoxin. Left: Using biotin tyramide, right using biotin-SS-tyramide. Clones giving ELISA signals >0.2 were considered as binders. Left: 3 clones, right 6 clones.

The present inventors show that screening of diverse libraries can be significantly accelerated using $^3$CARD via conversion of a transient interaction of an antibody with its antigen into a permanent label, i.e. covalent coupling of biotin to the surface of phage or microbial cells. This was achieved via application of a coupled enzyme reaction on the phage or yeast surface, where target-bound oxidase generates $H_2O_2$ that is required by phage bound peroxidase to activate biotin tyramide. Biotin tyramide has extensively been used in immunohistochemistry and also for selectively labelling enzyme displaying cells. Due to its short half-life in aqueous solutions the enzyme-formed tyramide radical reacts at the site of formation thus allowing for the site specific covalent deposition of biotin (Bobrow et al., 1989, 1991, 1992, Becker et al. 2007, 2008, Lipovsek et al. 2007).

For a genotype-phenotype linkage to occur, the biotinylation reaction has to be carefully controlled and restricted to the population of rare library members that are able to interact specifically with a predetermined interaction partner. To this end, a coupled enzyme reaction was established were the activity of tyramide radical forming HRP is controlled by the formation of hydrogen peroxide via an oxidase. In this case, the antigen-oxidase conjugate in solution is in vast excess over phage particles. However, production of excess $H_2O_2$ that is required by HRP to activate tyramide can be avoided by addition of catalase that efficiently and continuously breaks down hydrogen peroxide. Moreover, the coupling reaction is performed at a pH that is suboptimal for the respective oxidase to further reduce excess hydrogen peroxide. As a consequence, only HRP molecules that are in close proximity to an oxidase have a chance to capture a hydrogen peroxide molecule before it is decomposed by catalase. All together, the system inherits several layers of security to ensure selective biotin labelling of target bound phage both by making $H_2O_2$ exclusively available to HRP on antigen binding phage and generating a tyramide radical that due to its short half-life is acting locally.

To the best knowledge of the inventors this is for the first time that a coupled enzyme reaction is applied to phage display screening. A single enzyme approach to permanently label target binding bacteriophages has been described by McCafferty and coworkers over a decade ago. It was termed 'pathfinder technology' and relies on the HRP mediated biotinylation of antibody displaying phage at a specific site on a cell surface or target protein (Osbourn et al. 1998). In this experimental setup, the peroxidase was not directly coupled to phage particles. Instead, a peroxidase-conjugated ligand to the target protein, e.g. an antibody was used that binds the target protein apart from the phage antibody binding site. Colocalization of target bound phage and HRP on the target results in phage biotinylation. This method has been applied exclusively to cell surface exposed target proteins, which makes it possible to remove excess of peroxidase-ligand conjugate and unbound phage particles whether biotinylated or not by cell centrifugation and washing prior to phage capturing via binding to streptavidin beads. The method described here can be successfully applied to the screening of soluble targets, due to the strongly reduced cross-biotinylation of phage particles that are unable to bind the target protein by addition of catalase that eliminates excess of the peroxidase substrate hydrogen peroxide. Conversion of the transient interaction of binder and target protein into a covalent biotin label provides the main advantage that very stringent wash conditions for removal of phage that unspecifically bind to the adsorption matrix can be applied. We have used extensive wash procedures that include usage of detergents as well as lowering the pH to 2.2 since it is known that the biotin streptavidin interaction is stable under those conditions (Hofmann et al. 1980). It can be expected that at low pH the phage-bound target protein complex denatures and therefore dissociates which may be beneficial for phage infection of *E. coli* cells that requires an unmasked pill protein. Since we observed that phage particles that are bound to magnetic beads can be directly used for bacterial infection no efforts were made to disrupt the very stable biotin streptavidin interaction that even remains stable at pH 2.2 and to desorb the phage particles from the matrix. Usage of a biotin tyramide conjugate with a cleavable linker that allows for the selective release of biotinylated phage from the streptavidin matrix can further reduce the unwanted background of unspecifically bound phage.

The procedure described here yielded medium affinity binders. This was not unexpected since both libraries have already been used for VHH isolation applying conventional phage display (LibA) and yeast surface display (LibB) strategies yielding binders with similar affinities (data not shown). Moreover, LibB is derived from non-immunized llamas which per se is expected to contain a broad repertoire of low and medium affinity binders due to lack of affinity maturation in vivo. At present it remains to be experimentally elucidated whether $^3$CARD phage display screening allows for the discrimination between low and high affinity binders and therefore can be used for affinity maturation screening. Since the concentration of oxidase-target conjugate can be varied freely it may be feasible to screen for high affinity binders by affinity selection via reduction of target concentration or via off-rate selection (Hawkins, Russell 1992). For affinity selection, phage can be mixed with small amounts of soluble oxidase conjugated antigen such that the antigen is in excess over phage but with the concentration of antigen lower than the dissociation constant ($K_d$) of the antibody. Those phage bound to antigen are then labelled by $^3$CARD and isolated by capture to magnetic beads. For off-rate selection, antibodies can be preloaded with oxidase-coupled antigen and diluted into excess of unconjugated antigen prior to $^3$CARD capture on streptavidin-coated paramagnetic beads.

In conclusion, the strategy described here is particularly useful for the initial screening of very large phage or microbial display libraries exceeding $10^9$ different variants where it is important in the first screening rounds to enrich the rare target binders against a large background of non-specific phage. The genotype phenotype linkage via coupled enzyme reaction and reporter deposition may be also applicable to the screening of libraries that are displayed on the surface of bacterial and yeast cells with interesting ramifications for future applications.

The following examples are provided for illustration purposes, but are not meant to limit the scope of the invention in any way. Specially, specific new combinations of different embodiments set out in the examples and elsewhere in the description of the present invention are always contemplated even where they are not specifically mentioned.

EXAMPLE 1

Conjugation of Oxidase to Target Protein

Figure 6:
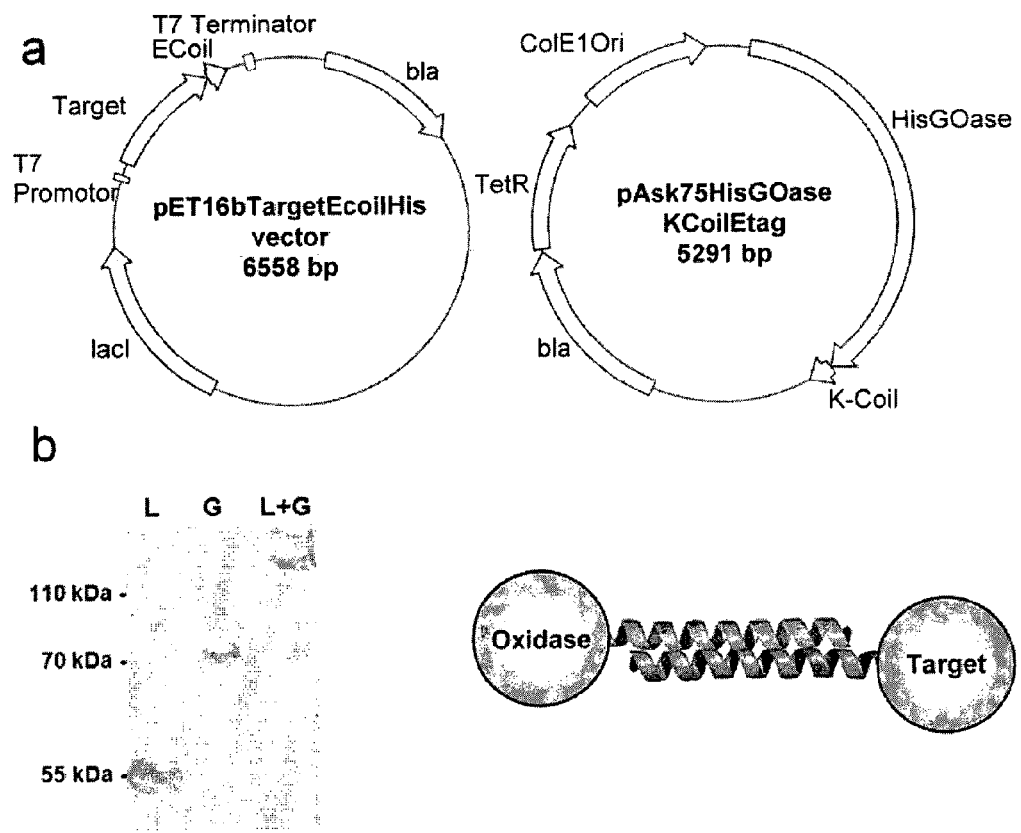
FIG. 6 shows (a) scheme of the production vectors, containing the coding sequences for the oxidase or target protein, respectively with genetically fused coil sequence. (b) Blue native gel without SDS containing the LipH-Oxidase (L+G, 160 kDa), LipH-Ecoil (L, 55 kDa) and GOase-Kcoil (G, 70 kDa). The model illustrates the formed conjugation product.
Figure 7:
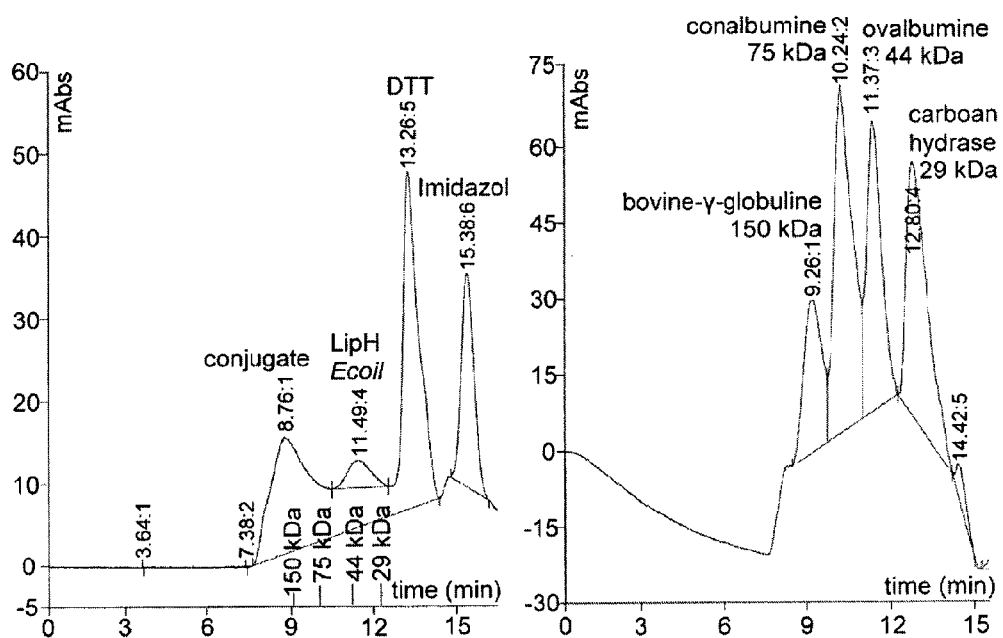
FIG. 7 shows a GFC chromatogram of the resulting fusion product of GOase-Kcoil and LipH-Ecoil.

Two straightforward coupling methods for covalent linkage of an oxidase and the target protein were established. The first conjugation scheme relies on the usage of the M1 variant of galactose oxidase (GOase) that can be expressed in *E. coli* (Sun et al. 2001). For target protein coupling to GOase, a previously established procedure was used that relies on coiled coil formation between enzyme and protein of interest. To this end, target protein and oxidase were endowed with a carboxyterminal hexahistidine tag followed by a coiled coil sequence containing glutamic acid (Ecoil) or lysine residues (Kcoil), which are known to form tight heterodimers (Steinman et al. 2010). The Ecoil sequence $(EVSALEK)_5$, SEQ ID NO:1, was genetically fused to LipH, and the Kcoil sequence $(KVSALKE)_5$, SEQ ID NO:2, was fused to the carboxy terminus of galactose oxidase. Both proteins were separately expressed in *E. coli* and purified. Heterodimer formation was achieved simply by mixing oxidase and LipH and confirmed by native polyacrylamide gel electrophoresis (FIGS. 6, 7). For an alternative conjugation method the commercially available glucose oxidase was used. Since this enzyme is glycosylated, protein conjugation with the target protein can easily be achieved by periodate oxidation of terminal sugar moieties followed by Schiff base formation of the resulting aldehyde with an lysine residue residing on the surface of the target protein (Greg T. Hermanson, 1996). To this end, oxidised glucose oxidase from *Fusarium* spec. was incubated with molar excess of LipH protein and the fusion was purified from unconjugated oxidase by metal chelate affinity chromatography making use of the hexahistidine tag of the LipH moiety (FIG. 8).

EXAMPLE 2

Coupled Enzyme Reaction on Phage

Figure 1:
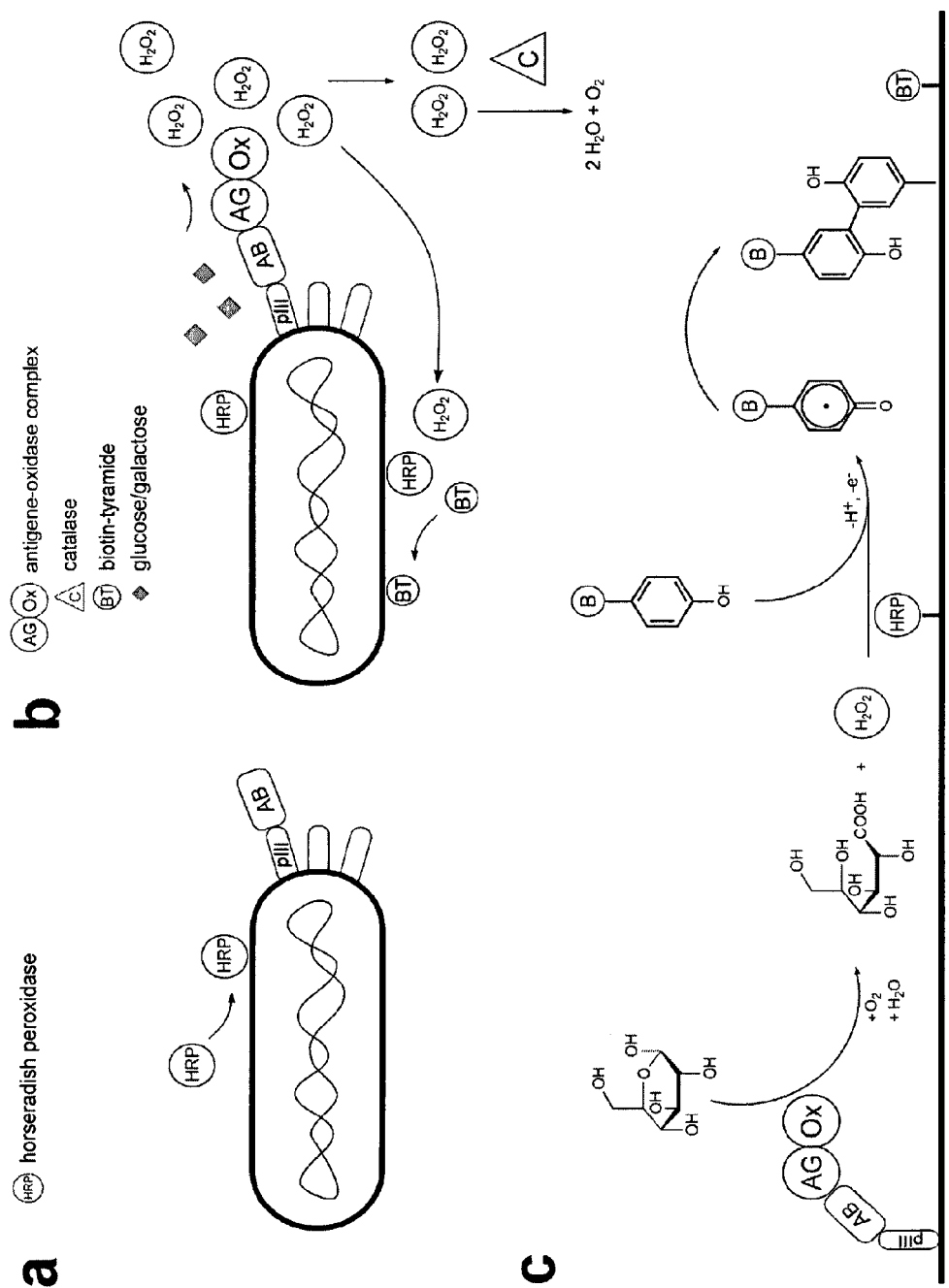
Figure 2:
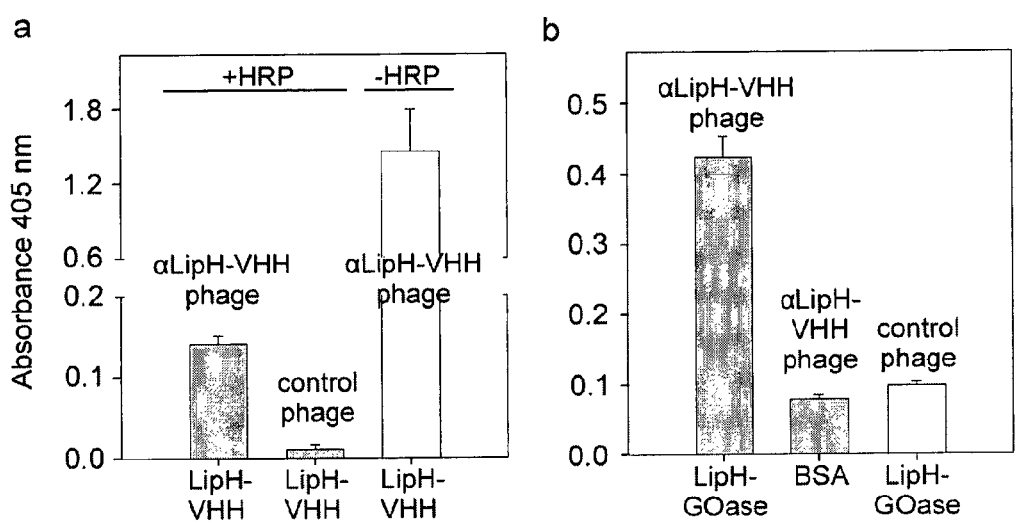

To investigate whether horseradish peroxidase (HRP) can be coupled to the surface of filamentous phage without negative interference with antigen binding, phage particles displaying anti-LIPH VHH and control phage displaying an unrelated peptide were incubated with oxidized HRP and purified via severalfold phage precipitation using polyethylene glycol. Wells of a microtiter plate were coated with LipH target protein. Binding of HRP coated phage that displayed an anti-LipH VHH antibody to immobilized antigen could be confirmed via measurement of peroxidase activity using the chromogenic substrate TMB (FIG. 2a). It remained to be elucidated whether a coupled reaction can occur on the phage surface where the oxidase delivers the hydrogen peroxide that is required by HRP, a microtiter plate was coated with LipH-GOase conjugate. HRP-coated phage displaying anti-LipH VHH or a control phage displaying an unrelated antigen, respectively were added. After washing and addition of galactose, peroxidase activity could be detected (FIG. 2b) indicating a coupled reaction to take place on phage.

EXAMPLE 3

Validation of Genotype-phenotype Coupling

Figure 3:
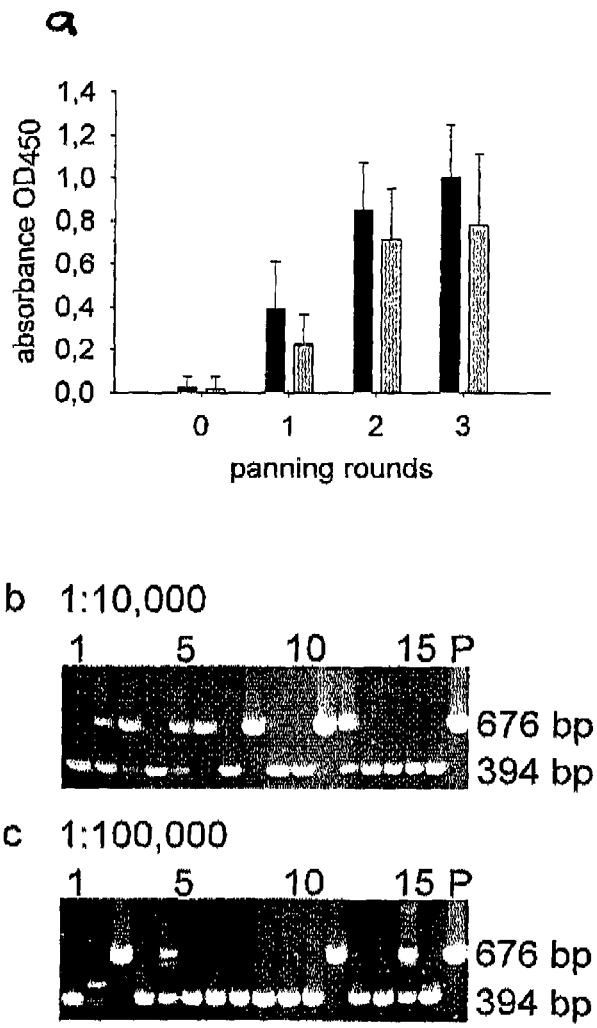

For the validation of genotype-phenotype coupling anti-LipH VHH presenting phage were mixed with control phage at a ratio of 1:10,000 and 1:100,000, respectively. After HRP conjugation and addition of the LipH-GOase complex the coupled enzyme reaction was started by addition of galactose, biotin tyramide and catalase. After 30 min incubation biotinylated phages were captured via binding to streptavidin-coated magnetic beads. After thorough washing with PBS, PSB-Tween and glycine buffer pH 2.2, respectively, phage-bound beads were used directly to infect E. coli cells. Two more rounds of the same screening procedure were applied and enrichment of anti-LipH-VHH presenting phage was verified by phage ELISA and PCR analysis. In both mixtures after a single screening round target binding phage accumulated to a significant extent (FIG. 3a). PCR analysis of individual clones after screening round 2 revealed that 6 out of 16 clones of the 1:10,000 dilution and 3 out of 16 clones of the 1:100,000 dilution contained a 676 bp fragment which is indicative of presence of the VHH gene. This mixing experiment was repeated several times with similar results to optimize the method protocol and to ensure its reproducibility. Enrichment depends on the presence of both biotin tyramide and galactose (FIG. 9)

EXAMPLE 4

$^3$CARD VHH Library Screening

Figure 4:
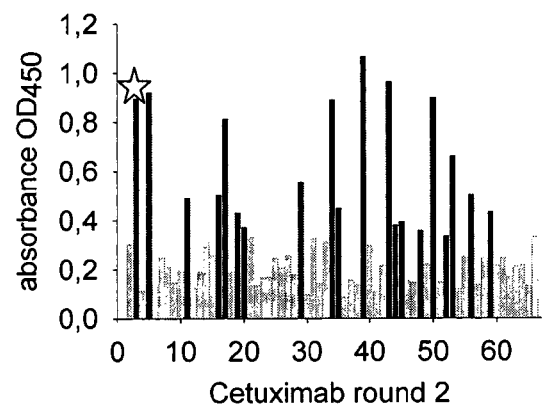
Figure 4:
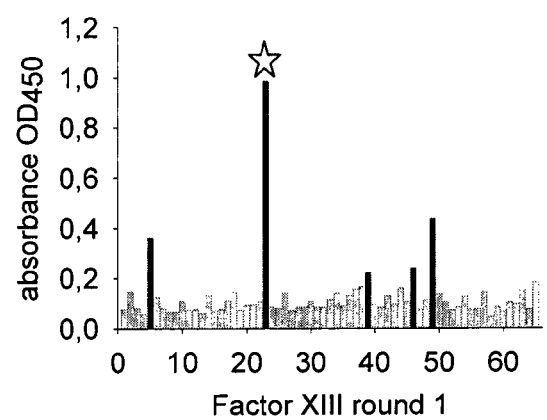
Figure 4:
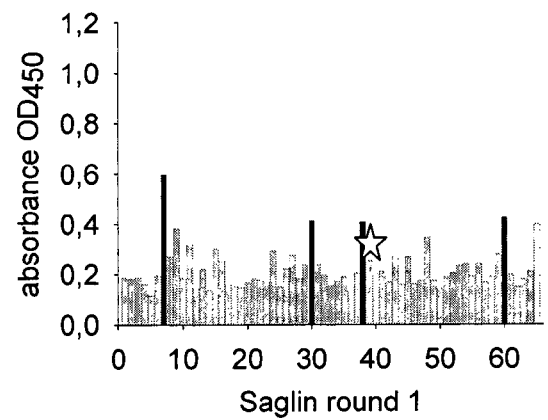

To investigate whether $^3$CARD phage display screening can be used for the fast selection of antigen binders from a phage library, two camelid VHH phage display libraries were used. LibA contains approximately $10^8$ variants of camelid variable heavy chains with randomly variegated hypervariable loop sequences (Habicht et al. 2007). LibB is a naïve VHH domain library ($3 \times 10^9$ clones) that was obtained via cloning the VHH repertoire of 12 non-immunized llamas into the phage display vector pAK200 using published procedures (Monegal at al. 2009). Three different target proteins that were coupled to glucose oxidase were used for screening, namely Cetuximab, an anti-epidermal growth factor receptor antibody (Robert et al. 2001), Saglin, a salivary gland protein from Anopheles that is involved in the process of invasion of mosquitoes by sporozoites of Plasmodium, the causative agent of malaria (Okulate et al. 2007), and factor XIII, a human transglutaminase that plays a role in blood coagulation (Komaromi et al. 2010). After screening round 1 or 2, respectively, phage were generated from 64 individual clones and probed for target protein binding via phage ELISA indicating accumulation of target binding phage clones for all three targets (FIG. 4).

The coding sequence of one putative binder from each screen was transferred to expression vector pEX and the respective VHH protein was produced and purified from E. coli cell lysate. Interaction with the respective target protein was verified by biolayer interferometry and dissociation constants in the mid nanomolar range were obtained (Table 1) corroborating the notion that the screening scheme is robust enough to obtain single domain antibodies from different libraries against several unrelated targets in one or two screening rounds. No efforts have been made to remove oxidase, peroxidase or phage protein binders from the initial phage library prior to screening that therefore may make up a significant fraction of the selected phage population.

TABLE 1

| I Dissociation constants ($K_d$) of VHHs obtained from $^3$CARD screening | | | | |
|---|---|---|---|---|
| Target antigen | Screening rounds | $K_d$ (nM) | library | # positive clones |
| Cetuximab | 2 | 156 | LibA + LibB | 8/32 + 12/32 |
| Factor XIII | 1 | 235 | LibB | 5/64 |
| Saglin | 1 | 90 | LibB | 4/64 |

EXAMPLE 5

Conjugation of Oxidase to Antigen Via Coiled Coil Formation

To obtain a heterodimer of oxidase and target antigen, P. aeruginosa LipH was expressed in E. coli with an C-terminal hexahistidine tag followed by an acidic coil (EVSALEK)$_5$, SEQ ID NO:1, encoding sequence (Steinmann et al 2010). Likewise, galactose oxidase M1 was endowed with a C-terminal hexahistidine purification tag followed by (KVSALKE)$_5$, SEQ ID NO:2. Both proteins were purified by metal chelate affinity chromatography and mixed in a molar 1:1 ratio prior to use for screening experiments.

EXAMPLE 6

Sodium Periodate Oxidation 18.8 mg sodium periodate (87.8 µmol, Sigma) were diluted in 1 ml H$_2$O. The protein to be oxidised, either HRP or glucose oxidase (Sigma), was diluted in H$_2$O to a final concentration of 10 mg/ml. For oxidation 200 µl protein solution was mixed with 20 µl of the sodium periodate stock solution. After 20 min incubation at RT in the dark, the reaction mixture was purified with a PD10 column (GE Healthcare) preequilibrated with 100 mM sodium borate buffer pH 9.1. 1.4 ml of the eluate containing the oxidised protein was filled up to 2 ml with sodium borate buffer and stored in aliquots at −20° C.

EXAMPLE 7

Target Protein Coupling to Glucose Oxidase 0.1 mg of periodate oxidized glucose oxidase at a concentration of 1 mg/ml were incubated with an equimolar amount or less equivalent of the target protein in 200 µl buffer at room temperature in the dark for 180 min followed by gel filtration chromatography using Superdex 75 pg 16/60 or Superdex 200 pg 16/60 column, respectively and collection of the early eluting fraction.

Critical Step: Conjugate formation should be checked either by native gel electrophoresis or by gel filtration chromatography. Since yields of heterodimer conjugate may vary depending on the number of accessible lysine residues on the surface of the target protein it is generally recommended to purify the conjugation product by gel filtration chromatography using a Sepharose or Superdex column by collecting the early eluting fractions.

EXAMPLE 8

HRP Coupling to M13 Phage

Prior to HRP coupling, streptavidin binders were removed from the phage library. To this end, 100 µl pAK200-VHH phages ($3*10^{10}$ phages) were incubated with 10 µl Streptavidin-Dynabeads (T1, Invitrogen) for 30 min at RT at 40 rpm in a shaker. After separation of the beads using a magnetic particle concentrator, the supernatant was transferred into a 1.5 ml reaction tube and 100 µl oxidized HRP (2 mg/ml in borate buffer pH 9.1) was added. The reaction mixture was incubated at room temperature in the dark under slow agitation for 45 min. To remove uncoupled HRP 200 µl phage precipitation buffer (20% PEG 6000, 1.5M NaCl) was added followed by incubation on ice for 45 min. After centrifugation in a table top centrifuge (30 min), the phage pellet was dissolved in 50 µl PBS.

EXAMPLE 9

Coupled Enzyme Reaction on Phage

5 µl (3 pMol) antigen-oxidase conjugate was added to 50 µl HRP conjugated phage suspension and incubated for 90 min at 4° C. with slight agitation. Then, the reaction volume was raised to 500 µl by addition of PBS buffer. When using GOase as reporter enzyme the pH was adjusted to 9.1 via addition of borate buffer. Then, 1 µl catalase (2 mg/ml) and 2.5 µl biotin tyramide stock solution (11.5 µM) were added. The enzyme reaction was started by addition of 10 µl 10 mM glucose or 10 µl 10 mM galactose, respectively. The reaction mixture was incubated for 15 min at RT in the dark and stopped by addition of 200 µl catalase (2 mg/ml). After three minutes 700 µl phage precipitation buffer was added and the mixture was incubated on ice for 45 min. The phage pellet was collected by centrifugation in a table top centrifuge (20 min, 4° C.) and resuspended in 200 µl PBS.

Critical Step: It is essential to lower the oxidase activity via performing the reaction at a pH that is suboptimal for the respective oxidase. To this end the coupled enzyme reaction on phage should be performed in borate buffer pH 9.1, when GOase is used, which is far beyond the pH optimum of the enzyme (pH 7.0) to slow down the enzymatic reaction and to avoid production of excess hydrogen peroxide. In case the glucose oxidase the pH optimum is 5.5 so the reaction should be performed in PBS pH 7.4. It is also important to add catalase which destroys excess hydrogen peroxide produced by the oxidase that is not bound to phage which may otherwise diffuse away from its place of formation and act as a substrate for peroxidase located on neighbouring phage particles.

EXAMPLE 10

Capturing of Biotinylated Phages

20 µl streptavidin coupled magnetic beads (Dynabeads T1, Invitrogen) were added to the sample and incubated by agitation for 30 min. Then the beads were washed five times with 200 µl PBS buffer. A magnetic particle collector was used to separate beads from the supernatant. Afterwards the collected beads were suspended in 200 µl PBS buffer and transferred to a new tube to eliminate potentially plastic binding antibody-phages. Beads were collected and resuspended in 200 µl 10 mM glycine-HCl pH 2.2 and incubated for 8 min to remove unspecifically bound phages from the beads. This procedure was repeated once. Finally, beads were washed five times using PBS Tween buffer (0.05% Tween 20 in PBS buffer) and five times with PBS buffer.

EXAMPLE 11

Infection of *E. coli* Cells

After the last wash step, streptavidin-coated beads with bound phage were resuspended in 200 µl PBS and used for infection of *E. coli* ER 2738 via dilution into 20 ml bacterial liquid culture at an $OD_{600}$ of 0.5 and incubated for 30 min at 37° C. without shaking. Cells were collected by centrifugation, dissolved in 1.5 ml PBS and streaked out in 500 µl aliquots on agar plates containing chloramphenicol (25 µg/ml) and incubated overnight at 37° C.

EXAMPLE 12

General Methods for Phage Production

*E. coli* strain ER2738 (Gough 1983, Woodcock 1989) containing phagemid pAK200-VHH was grown to an $OD_{600}$ of 0.1 in 50 ml dYT (CM 25 µg/ml, TET 100 µg/ml) at 37° C. (shaking, 200 rpm) and 10 µl of helper phage M13VCS were added. The infection was performed by incubating the cells for 45 minutes at 37° C. Kanamycin (75 µg/ml) was added and the culture was incubated at 37° C. (200 rpm) until an $OD_{600}$ of 0.5 was reached. Then, 50 µl 1 M IPTG was added for induction of VHH-pIII synthesis and incubation was continued for 12 h at 28° C. The produced phages were harvested by phage precipitation. To this end, cells were collected by centrifugation (3200 g, 12 min, 4° C.) and 35 ml of the supernatant were transferred to a 50 ml high speed falcon tube. 8 ml phage precipitation buffer (20% PEG 6000, 1.5 M NaCl) was added and the mixture was incubated for 4 hours on ice. Precipitated phage were collected by centrifugation (20200 g, 4° C., 30 min). The resulting phage pellet was dissolved in 1.6 ml PBS and phage were re-precipitated by addition of 400 µl precipitation buffer by incubation for 10 min at 4° C.). After centrifugation (16000 g, 10 min, RT) the remaining phage pellet was dissolved in 1 ml PBS. Phage titer was determined by ER2738 infection of a serial dilution of phage particles or spectrometrically via determination of $OD_{320}$ and $OD_{269}$ (Smith, Scott 1993). Phages were stored at 4° C. until further use.

TABLE 2

Phage titer of VHHs obtained from 3CARD screening.

| target antigen | library | round | start phages | infection count | collected (%) |
|---|---|---|---|---|---|
| Cetuximab | LibA | 1 | $3 \cdot 10^{11}$ | $8.4 \cdot 10^6$ | 0.0028 |
|  |  | 2 | $1 \cdot 10^{10}$ | $2.4 \cdot 10^6$ | 0.024 |
| Factor XIII | LibB | 1 | $1 \cdot 10^{12}$ | $9.5 \cdot 10^5$ | 0.000095 |
| Saglin | LibA | 1 | $5 \cdot 10^{11}$ | $1.9 \cdot 10^4$ | 0.0000038 |
| Saglin | LibB | 1 | $1 \cdot 10^{12}$ | $1.9 \cdot 10^4$ | 0.0000019 |

| target antigen | library | round | start phages (a) | infection count (b) | ratio (a/b) |
|---|---|---|---|---|---|
| Cetuximab | LibA | 1 | $3 \cdot 10^{11}$ | $8.4 \cdot 10^6$ | $3.6 \cdot 10^4$ |
|  |  | 2 | $1 \cdot 10^{10}$ | $2.4 \cdot 10^6$ | $4.2 \cdot 10^3$ |
| Factor XIII | LibB | 1 | $1 \cdot 10^{12}$ | $9.5 \cdot 10^5$ | $1.1 \cdot 10^6$ |
| Saglin | LibA | 1 | $5 \cdot 10^{11}$ | $1.9 \cdot 10^4$ | $2.6 \cdot 10^7$ |
| Saglin | LibB | 1 | $1 \cdot 10^{12}$ | $1.9 \cdot 10^4$ | $5.2 \cdot 10^7$ |

EXAMPLE 13

Figure 5:
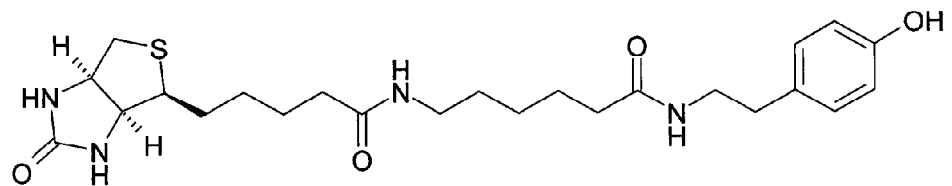
FIG. 5 shows the chemical structure of biotin tyramide.

Synthesis of Biotin Tyramide 10 mg (17.96 µmol) Sulfo-NHS-LC-biotin (Thermo Scientific) were diluted in 800 µl dry DMF and mixed with a solution of 2 mg (11.51 µmol) tyramide (Sigma-aldrich) in 200 µl dry DMF. Then 3 µl triethylamine was added and the reaction mixture was incubated for 2 h at RT. To quench the remaining excess of Sulfo-NHS-LC-biotin (Pierce) 20 µl 1-propylamine were added to the solution. After 4 h of incubation at RT the resulting product was stored at −20° C. without further purification. Formation of biotin-tyramide was confirmed by HPLC and LC-MS. The chemical structure of biotin tyramide is shown in FIG. 5.

EXAMPLE 14

Comparison with State of the Art Phage Display

To show that the phage library screening method of the present invention is superior to the state of the screening method, classical screening and 3CARD screening were performed in parallel using identical screening conditions. Targets: Cetuximab and LipH (targets have already been described in the invention as well as the screening methodology). 3CARD screening was performed as described for one screening round. For classical screening, biotinylated target protein at the same concentration as for 3CARD (4.5 nM) was used. Phage library was incubated with biotinylated target protein at RT. After 20 min, target binding phage were captured to streptavidin coated magnetobeads (15 min). After washing the beads 10 times with 1 ml TPBS remaining bound phage were eluted with glycine buffer pH 2.2 and used for infection of E. coli cells. After one screening round phages were prepared from 96 individual clones and probed for their ability to bind the respective target protein using a phage ELISA. Results are shown in FIGS. 11 and 12.

EXAMPLE 15

Further Preferred Embodiment of the 3CARD Technology

As a new compound for labeling target binding phage a biotin tyramide derivative was used that contains between the biotin and the tyramide moiety of the linking molecule a disulfide bond. As a consequence, from a labeled phage the biotin moiety can be cleaved off via addition of a mild reducing agent as e.g. dithiotreitol.

Synthesis of Biotin Tyramide 10 mg (17.96 µmol) Sulfo-NHS-LC-biotin respectively Sulfu-NHS-SS-biotin (Thermo Scientific) were diluted in 800 µl dry DMF and mixed with a solution of 2 mg (11.51 µmol) tyramide (Sigma-aldrich) in 200 µl dry DMF. Then 3 µl triethylamine was added and the reaction mixture was incubated for 2 h at RT. To quench the remaining excess of Sulfo-NHS-LC-biotin respectively Sulfo-NHS-SS-biotin 20 µl 1-propylamine were added to the solution. After 4 h of incubation at RT the resulting product was stored at −20° C. without further purification. Formation of biotin tyramide was confirmed by HPLC and LC-MS.

Three additional screens for target binding phages were performed using this novel labeling molecule. As target proteins, the E. coli protein MreB, human CTLA4 (Cytotoxic T-Lymphocyte Antigen 4) extracellular domain and thioredoxin were used.

For phage library screening, the same phage library was used as already described. Also the target-oxidase coupling was performed as described. After phage labeling, biotinylated phages were captured to streptavidin coated magnetobeads. After thorough washing, captured phage were directly used for infection of E. coli cells in case of usage of biotin tyramide (FIG. 14-16, left panel). For phages that were labeled using biotin-SS-tyramide, magnetobead bound phage particles were cleaved off via addition of 50 mM dithiotreitol as reducing agent. Eluted phage were then used to infect E. coli cells. For each screen, phages were prepared from 96 single clones and probe for their ability to bind the respective target protein using a phage ELISA.

The screens provide target binding phage already after one single screening round. Using the improved substrate and improved phage isolation procedure, the number of positive candidates increased to a higher number.

BIBLIOGRAPHY

Bayer, E. A., Ben-Hur, H., Gitlin, G. & Wilchek, M. (1986): An improved method for the single-step purification of streptavidin. J Biochem Biophys Methods. 13: 103-112.

Becker, S., Michalczyk, A., Wilhelm, S., Jaeger, K. E. & Kolmar, H. (2007): Ultrahigh-throughput screening to identify *E. coli* cells expressing functionally active enzymes on their surface. Chembiochem. 8: 943-949.

Becker S, Höbenreich H, Vogel A, Knorr J, Wilhelm S, Rosenau F, Jaeger K E, Reetz M T, Kolmar H. (2008) Single-cell high-throughput screening to identify enantioselective hydrolytic enzymes. Angew Chem Int Ed Engl. 47(27):5085-8.

Bobrow, M. N., Harris, T. D., Shaughnessy, K. J. & Litt, G. J. (1989): Catalyzed reporter deposition, a novel method of signal amplification. Application to immunoassays. J Immunol Methods. 125: 279-285.

Bobrow, M. N., Litt, G. J., Shaughnessy, K. J., Mayer, P. C. & Conlon, J. (1992): The use of catalyzed reporter deposition as a means of signal amplification in a variety of formats. J Immunol Methods. 150: 145-149.

Bobrow, M. N., Shaughnessy, K. J. & Litt, G. J. (1991): Catalyzed reporter deposition, a novel method of signal amplification. II. Application to membrane immunoassays. J Immunol Methods. 137: 103-112.

Bradbury A R, Sidhu S, Dübel S, McCafferty J. (2011) Beyond natural antibodies: the power of in vitro display technologies. Nat. Biotechnol. 29:245-54.

Brockmann, E. C., Akter, S., Savukoski, T., Huovinen, T., Lehmusvuori, A., Leivo, J., Saavalainen, O. et al. (2011): Synthetic single-framework antibody library integrated with rapid affinity maturation by VL shuffling. Protein Eng Des Sel. 24: 691-700.

Derda, R., Tang, S. K., Li, S. C., Ng, S., Matochko, W. & Jafari, M. R. (2011): Diversity of phage-displayed libraries of peptides during panning and amplification. Molecules. 16: 1776-1803.

Gitlin, G., Bayer, E. A. & Wilchek, M. (1990): Studies on the biotin-binding sites of avidin and streptavidin. Tyrosine residues are involved in the binding site. Biochem J. 269: 527-530.

Gough et al. (1983): Sequence diversity among related genes for recognition of specific targets in DNA molecules. Journal of Molecular Biology 166: 1-9.

Green, N. M. (1975): Avidin. Adv Protein Chem. 29: 85-133.

Habicht, G., Haupt, C., Friedrich, R. P., Hortschansky, P., Sachse, C., Meinhardt, J., Wieligmann, K. et al. (2007): Directed selection of a conformational antibody domain that prevents mature amyloid fibril formation by stabilizing Abeta protofibrils. Proc Natl Acad Sci USA. 104: 19232-19237.

Hawkins, R. E., Russell, S. J. & Winter, G. (1992): Selection of phage antibodies by binding affinity. Mimicking affinity maturation. J Mol. Biol. 226: 889-896.

Hermanson, G. T. Bioconjugation techniques. (Academic Press, 1996).

Hofmann, K., Wood, S. W., Brinton, C. C., Montibeller, J. A. & Finn, F. M. (1980): Iminobiotin affinity columns and their application to retrieval of streptavidin. Proc Natl Acad Sci USA. 77: 4666-4668.

Hoogenboom, H. R. (2005): Selecting and screening recombinant antibody libraries. Nat. Biotechnol. 23: 1105-1116.

Komaromi, I., Bagoly, Z. & Muszbek, L. (2010): Factor XIII: novel structural and functional aspects. J Thromb Haemost. 9: 9-20.

Li, W. & Caberoy, N. B. (2010): New perspective for phage display as an efficient and versatile technology of functional proteomics. Appl Microbiol Biotechnol. 85: 909-919.

Lipovsek D, Antipov E, Armstrong K A, Olsen M J, Klibanov A M, Tidor B, Wittrup K D. (2007) Selection of horseradish peroxidase variants with enhanced enantioselectivity by yeast surface display. Chem. Biol. 14(10): 1176-85.

Liu, Y., Adams, J. D., Turner, K., Cochran, F. V., Gambhir, S. S. & Soh, H. T. (2009): Controlling the selection stringency of phage display using a microfluidic device. Lab Chip. 9: 1033-1036.

Monegal, A., Ami, D., Martinelli, C., Huang, H., Aliprandi, M., Capasso, P., Francavilla, C., Ossolengo, G. & de Marco, A. (2009): Immunological applications of single-domain llama recombinant antibodies isolated from a naive library. Protein Eng Des Sel. 22: 273-280.

Okulate, M. A., Kalume, D. E., Reddy, R., Kristiansen, T., Bhattacharyya, M., Chaerkady, R., Pandey, A. & Kumar, N. (2007): Identification and molecular characterization of a novel protein Saglin as a target of monoclonal antibodies affecting salivary gland infectivity of *Plasmodium* sporozoites. Insect Mol. Biol. 16: 711-722.

Pepper L R, Cho Y K, Boder E T, Shusta E V. (2008) A decade of yeast surface display technology: where are we now? Comb Chem High Throughput Screen. 11(2):127-34.

Osbourn, J. K., Derbyshire, E. J., Vaughan, T. J., Field, A. W. & Johnson, K. S. (1998): Pathfinder selection: in situ isolation of novel antibodies. Immunotechnology. 3: 293-302.

Osbourn, J. K., Earnshaw, J. C., Johnson, K. S., Parmentier, M., Timmermans, V. & McCafferty, J. (1998): Directed selection of MIP-1 alpha neutralizing CCR5 antibodies from a phage display human antibody library. Nat. Biotechnol. 16: 778-781.

Robert, F., Ezekiel, M. P., Spencer, S. A., Meredith, R. F., Bonner, J. A., Khazaeli, M. B., Saleh, M. N. et al. (2001): Phase I study of anti-epidermal growth factor receptor antibody cetuximab in combination with radiation therapy in patients with advanced head and neck cancer. J Clin Oncol. 19: 3234-3243.

Rothe, C., Urlinger, S., Lohning, C., Prassler, J., Stark, Y., Jager, U., Hubner, B. et al. (2008): The human combinatorial antibody library HuCAL GOLD combines diversification of all six CDRs according to the natural immune system with a novel display method for efficient selection of high-affinity antibodies. J Mol. Biol. 376: 1182-1200.

Smith, G. P. (1985): Filamentous fusion phage: novel expression vectors that display cloned antigens on the virion surface. Science. 228: 1315-1317.

Steiner, D., Forrer, P. & Pluckthun, A. (2008): Efficient selection of DARPins with sub-nanomolar affinities using SRP phage display. J Mol. Biol. 382: 1211-1227.

Steinmann, B., Christmann, A., Heiseler, T., Fritz, J. & Kolmar, H. (2010): In vivo enzyme immobilization by inclusion body display. Appl Environ Microbiol. 76: 5563-5569.

Sun, L., Petrounia, I. P., Yagasaki, M., Bandara, G. & Arnold, F. H. (2001): Expression and stabilization of galactose oxidase in *Escherichia coli* by directed evolution. Protein Eng. 14: 699-704.

van Bloois E, Winter R T, Kolmar H, Fraaije M. W. (2011) Decorating microbes: surface display of proteins on *Escherichia coli*. Trends Biotechnol. 29(2):79-86.

Vodnik, M., Zager, U., Strukelj, B. & Lunder, M. (2011): Phage display: selecting straws instead of a needle from a haystack. Molecules. 16: 790-817.

Wilhelm, S., Rosenau, F., Becker, S., Buest, S., Hausmann, S., Kolmar, H. & Jaeger, K. E. (2007): Functional cell-surface display of a lipase-specific chaperone. Chembiochem. 8: 55-60.

Woodcock, D. M., Crowther, P. J., Doherty, J., Jefferson, S., DeCruz, E., Noyer-Weidner, M., Smith, S. S., Michael, M. Z. & Graham, M. W. (1989): Quantitative evaluation of *Escherichia coli* host strains for tolerance to cytosine methylation in plasmid and phage recombinants. Nucleic Acids Res. 17: 3469-3478.

that is utilized by said first enzyme to convert a cosubstrate of said first enzyme into a reactive marker molecule that physically links to the respective replicating entity, thereby specifically labelling the replication entity, and d) isolating the specifically labelled replicating entities.

The invention claimed is:

1. A method for the isolation of specifically labelled replicating entities, said method comprising
    a) providing in a reaction mixture a collection of replicating entities displaying variants of a receptor molecule on their surface and having either a first or a second enzyme linked to said surface, the reaction mixture of step a) comprising a third enzyme capable of decomposing excess product of said first and/or second enzyme, the first enzyme being a peroxidase, the second enzyme being an oxidase, and the third enzyme being a catalase, the substrate of the second enzyme being glucose and the product being $H_2O_2$, the cosubstrate of said first enzyme being a tyramide conjugated to a marker molecule,
    b) adding to the mixture of step a) ligand molecules that are either linked to said first enzyme if said entities are linked to said second enzyme, or said ligands are linked to said second enzyme if said entities are linked to said first enzyme,
    c) adding to the reaction mixture a substrate for the second enzyme, the substrate being utilized by said second enzyme in an enzymatic reaction to produce a product 2. Method according to claim 1, wherein the replicating entity is selected from the group consisting of a phage, a phagemid, or a cell.

3. Method according to claim 2, wherein the replicating entity is a yeast cell.

4. Method according to claim 3, wherein the yeast cell is *Saccharomyces cerevisiae*.

5. Method according to claim 1, the tyramide being linked to the marker molecule by a cleavable linker.

6. Method according to claim 5, wherein the cleavable linker is a disulfide bond or a peptide sequence that can be cleaved by a protease.

7. Method according to claim 1, the marker molecule being biotin, (2,4)-dinitrophenyl, fluorescein or digoxygenin derivative.

8. Method according to claim 6, wherein the disulfide bond or a peptide sequence that can be cleaved by a protease is a Biotintyramide with cleavable disulfide bond of the following structure:

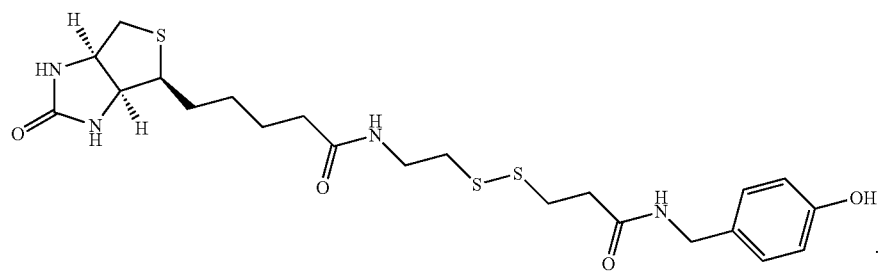 [SMILES: O=C(CCCC[C@@H]1SC[C@@H]2NC(=O)N[C@@H]21)NCCSSCCC(=O)NCc1ccc(O)cc1]

9. Method according to claim 1, the marker molecule being biotin, and the isolation step d) being accomplished by affinity chromatography on an avidin or streptavidin matrix.

10. Method according to claim 1, the marker molecule being fluorescein or a fluorescent avidin or strepatvidin bound biotin and the isolation step e) being accomplished by fluorescence activated cell sorting.

11. Method according to claim 1, wherein the marker molecule is biotin and the isolation comprises magnetic cell sorting in of streptavidin of avidin coated paramagnetic particles bound to the biotin labelled entity.

12. Method according to claim 1 wherein the receptor molecule is an antibody.

13. Method according to claim 12 wherein the antibody is Cetuximab.

* * * * *